United States Patent [19]

Kastron et al.

[11] Patent Number: 4,738,965
[45] Date of Patent: Apr. 19, 1988

[54] 2-OXO-4-(2'-DIFLUOROMETHYLTHIO-PHENYL)-5-METHOXYCARBONYL-6-METHYL-1,2,3,4-TETRAHYDROPYRIMIDINE

[75] Inventors: Valeria V. Kastron; Rasma O. Vitolin; Elena L. Khanina; Gunar Y. Dubur; Agris A. Kimenis, all of Riga; Natalya V. Kondratenko, Kiev; Vladimir Popov, Kiev; Lev M. Yagupolsky, Kiev; Alexandr A. Kolomeitsev, Kiev, all of U.S.S.R.

[73] Assignees: Institut Organischskogo Sinteza Akademii Nauk SSR, Riga; Institut Organicheskoi Khimii Akademii Nauk Ukrainskoi SSR, Kiev, both of U.S.S.R.

[21] Appl. No.: 10,393

[22] Filed: Feb. 3, 1987

[51] Int. Cl.⁴ .................. C07D 239/36; A61K 31/505
[52] U.S. Cl. ..................................... 514/274; 544/318
[58] Field of Search ......................... 514/274; 544/318

[56] References Cited

U.S. PATENT DOCUMENTS 4,675,321 6/1987 Baldwin et al. ..................... 544/318

OTHER PUBLICATIONS

Konyukhov et al., Zh. Organo Khim., vol. 1, No. 8, pp. 1487–1489 (1965).
Elkasaby, Pakistan J. Sci. Ind. Res., vol. 21, pp. 58–61 (1978).

Primary Examiner—John M. Ford
Attorney, Agent, or Firm—Burgess, Ryan & Wayne

[57] ABSTRACT

The present invention relates to organic chemistry.

The novel compound 2-oxo-4-(2'-difluoromethylthio-phenyl)-5-methoxycarbonyl-6-methyl-1,2,3,4-tetrahydropyrimidine has the formula:

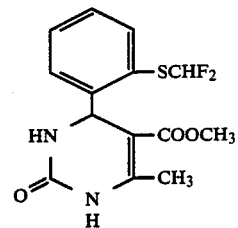

Said compound displays coronary-dilating activity and can be utilized in medicine.

3 Claims, No Drawings

2-OXO-4-(2'-DIFLUOROMETHYLTHIOPHENYL)-5-METHOXYCARBONYL-6-METHYL-1,2,3,4-TETRAHYDROPYRIMIDINE

FIELD OF APPLICATION OF THE INVENTION

The present invention relates to organic chemistry and more particularly it relates to the method for preparation of a new compound 2-oxo-4-(2'-difluoromethylthiophenyl)-5-methoxycarbonyl-6-methyl-1,2,3,4-tetrahydropyrimidine displaying a coronary dilating effect and intended for use in medicine.

BACKGROUND OF THE INVENTION

Known in the prior art are amides of 2-oxo-1,2,3,4-tetrapyrimidine-5-carboxylic acid displaying a coronary dilatation effect. (Inventor's Certificate of the USSR No. 422735, Cl.CO7d 51/34 (1974)). Experimentally administered to narcotized cats in doses of 1-2 mg/kg they increase the coronary blood flow by 20-40%. In addition, there are previously known β-aminoethyl ethers of 2-oxo-4-aryl-6-methyl-1,2,3,4-tetrahydropyrimidine-5-carboxylic acid displaying an insignificant hypotensive effect and bearing no influence on coronary blood flow (E. L. Khanina, G. O. Silenietse, Ya. Ya. Ozols, G. Ya. Dubur, A. A. Kimenis. Chemic-Pharmaceutical Journal 1978, No. 10, pp 72-74).

Known in the prior art is a coronary dilating preparation nifedipin-2,6-dimethyl-3,5-dimethoxycarbonyl-4-(2-nitrophenyl)-1,4-dihydropyrimidine, widely utilized in clinical practice.

This preparation, unfortunately, is not sufficiently nontoxic which, in turn, fails to ensure complete safety of its administration. For example, in 10% of patients nifedipin causes side effects such as dizziness, nausea, allergic reactions, and has a considerable hypotensive effect which is undesirable in some cases. Besides, nifedipin is difficult to handle since it is non-resistant to light and quickly decomposes in light, particularly in solutions.

Papaverine, a preparation widely used in clinical practice has but a low coronary dilating activity. The desired therapeutical effect calls for administration of large doses of papaverine. However, such large doses of the preparation are extremely undesirable because toxicity of papaverine is rather high.

The hereinproposed compound is novel, thus far not described in literature.

BRIEF DESCRIPTION OF THE INVENTION

The object of the present invention resides in preparation of a new compound displaying a high coronary dilating activity and low toxicity.

In accordance with this and other objects, the invention is comprised of the compound 2-oxo-4-4(2'-difluoromethylthiphenyl)-5-methoxycarbonyl-6-methyl-1,2,3,4-tetrahydropyrimidine which has the following formula

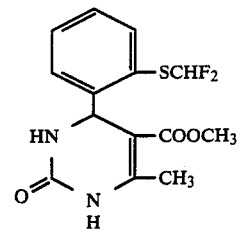

DETAILED DESCRIPTION OF THE INVENTION

Known in the art are methods for preparation of substituted tetrahydropyrimidines, e.g. 2-keto-1,2,3,4-tetrahydropyrimidine (cf K. Tolkas, H. J. Hardwood, T. B. Johnson, J. Am. Chem. Soc. 1932, V54, 3751-3758). The method is based on interaction of aldehyde of an β-keto ether with urea in a solution of alcohol.

The present method for preparation of 2-oxo-4-(2'-difluoromethylthiophenyl)-5-methoxycarbonyl-6-methyl-1,2,3,4-tetrahydropyrimidine is not described in the literature.

An object of the present invention is a method for preparation of a novel compound characterized by a high coronary dilatation effect and low toxicity.

This object has been attained according to the invention by the providing of a method for preparation of the claimed compound 2-oxo-4-(2'-difluoromethylthiphenyl)-5-methoxycarbonyl-6-methyl-1,2,3,4-tetrahydropyrimidine of the formula:

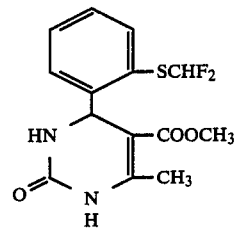

in which methyl ester of acetoacetic acid is made to interact with 2-difluoromethylthiobenzaldehyde and urea in an organic solvent in the presence of an acid acting as a catalyst, followed by separation of the end product.

The hereinproposed compound is a colourless crystalline substance insoluble in water, comparatively easily-soluble in ethyl alcohol, acetone, chloroform and other organic solvents. The compound is chemically stable.

The biological activity of the proposed compound has been studied in experiments on animals.

Investigations have been conducted of the coronary dilating and hypotensive effect and acute toxicity of the proposed compound in comparison with the known highly-intensive coronary dilating and hypotensive preparations, i.e. nifedipin and papaverine.

The proposed compound has been investigated by experimenting on rats and dogs.

The experiments have been conducted on narcotized dogs with the open thoracic cavity. The blood flow was registered in the descending branch of the left coronary artery.

The blood flow was determined before and after the injection of the proposed compounds. The proposed compound was introduced in a single dose, intravenously, followed by calculating the increase in the coronary blood flow in percent.

The results of investigations of the coronary dilating activity appear in Table 1, below.

TABLE 1

Effect of the Proposed Compound on Coronary Blood Flow Obtained in Experiments on Narcotized Dogs

| Compound 1 | Dose, mg/kg 2 | Increase of coronary blood flow, % 3 | Duration of effect, in 4 | Dose increasing coronary blood flow by 50%, mg/kg 5 |
|---|---|---|---|---|
| Proposed compound | 0.001 | 19 | 8 | 0.006 |
| Proposed compound | 0.01 | 79 | 35 | |
| | 0.1 | 107 | 60 | |
| Nifedipin | 0.01 | 78 | 20 | 0.007 |
| Papaverine | 0.1 | 20 | 5 | 0.9 |
| | 0.5 | 30 | 7 | |

One can conclude on the basis of Table 1 that the proposed compound, beginning with a 0.001 mg/kg dose increases the blood flow through the vessels by 19% within 8 minutes. Raising the dose up to 0.01–0.1 mg/kg increases the coronary blood flow by 79–107% in the course of 35–60 min, respectively. These doses of the proposed compound did not change the systemic arterial pressure and the cardiac output. With respect to the coronary dilating effect the investigated compound is approximately equal in activity to nifedipin. If we compare the doses the activity of the proposed compound is 150 times as high as that of papaverine. Besides, the investigated compound surpasses the known preparations with regard to the duration of its effect: 1.7 times compared with nifedipin and over 10 times compared with papaverine.

Besides, we have investigated the hypotensive activity of the proposed compound in comparison with nifedipin and papaverine. The experiments were conducted on spontaneously-hypertensive rats (SHR) of Okamoto-Aoki line. The proposed compound, nifedipin and papaverine were introduced into the stomach in a single 10 mg/kg dose.

The results of investigations of the hypotensive activity of the proposed compound compared to the known preparations are presented in Table 2.

TABLE 2

Effect of Proposed Compound on Arterial Pressure

| Compound | Hypotensive activity | Duration of hypotensive effect, h |
|---|---|---|
| Proposed compound | 8 | 6 |
| Nifedipin | 44 | 6 |
| Papaverine | 5 | 3 |

Table 2 reveals that the proposed compound introduced in a single dose into the stomach produced a small reduction (8%) of systolic arterial pressure observed in the course of 6 h. The same doses of nifedipin were observed to reduce arterial pressure by a far greater, by 44%. Papaverine exerts but an insignificant effect on arterial pressure (a 5% reduction of pressure).

Acute toxicity of the proposed compound compared with nifedipin and papaverine was investigated during experiments on mongrel white mice (weighing 20–24 g) by intraperitoneal injection administered to a group of 6 animals. Injection of a 2000 mg/kg dose did not result in fatal termination within the term of observation (2 weeks, which means that $LD_{50}$ of the proposed compound is over 2000 mg/kg, that of nifedipin is 185 mg/kg and papaverine, 91 mg/kg).

Thus, the proposed compound features a number of advantages over the known preparations:

strong and prolonged vasodilating effect with relation to coronary vessels: 1.7 times higher than nifedinpin and about 10 times higher than papaverine;

as distinct from nifedipin, the proposed compound bears no substantial effect on arterial pressure;

the proposed compound is noted for a low toxicity (10–20 times lower than that of nifedipin and papaverine thus ensuring a wide range of its therapeutic effect.

The proposed compounds are obtained through interaction of acetoacetic acid, urea and 2-difluoromethylthiobenzaldehyde in an organic solvent in the presence of catalytic quantities of hydrochloric or acetic acids. The process is carried on at room temperature with subsequent separation of the end product.

The process is shown by the following scheme:

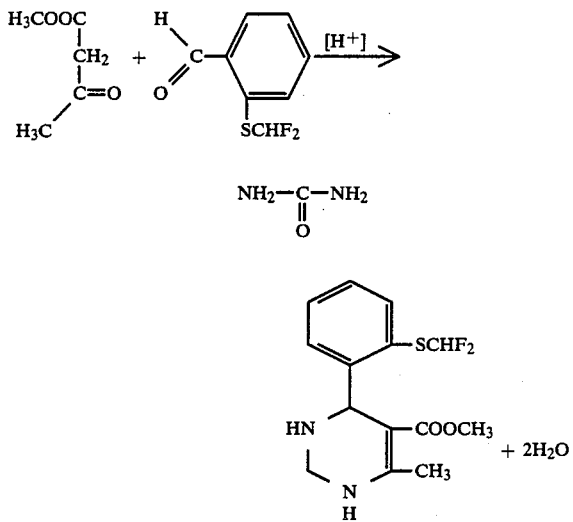

It is practicable to use ethanol as the organic solvent and hydrochloric or acetic acid as the acid component.

Now the invention will be made more apparent by the following examples of preparation of the proposed compound:

EXAMPLE 1

1.7 g (0.001 mole) of 2-difluoromethylthiobenzaldehyde, 1.17 g (0.001 mole) of methyl ether of acetoacetic acid, 0.6 g (0.001 mole) of urea are dissolved in 10 ml of ethanol, adding 5 drops of concentrated hydrochloric acid. The obtained mixture is left overnight. The precipitate is filtered and recrystallized from ethanol. The yield is 1.7 g (52.1%) of colourless crystals of 2-oxo-4-(2'-difluromethylthiophenyl)-5-methoxycarbonyl-6-methyl-1,2,3,4-tetrahydropyrimidine. M.p. 212°–214° C.

Found, %: C 50.85; H 4.66; N 8.26; $C_{14}H_{14}N_2O_3F_2S$.
Calculated, %: C 51.21; H 4.30; N 8.53.

$R_f$ 0.77 (acetone-hexane 1:1).

UV spectrum is reference standard, $\lambda_{max}$, nm (log $\epsilon$): 227 (3.78) 291 (9.78).

IR spectrum in vaseline oil, $cm^{-1}$: 3229, 3102, 1710, 1700, 1664, 1650.

PMR spectrum in CDCl3, δ, p.p.m. 2.42s (3H, 6-CH3); 3,54s (3H, OCH3); 5,47s (1H, NH); 6,1 d (1H, 4-H); 6,36t (1H, CHF2), J=57 Hz, 7,42m; (4H, ArH), 7,9C (1H, NH).

EXAMPLE 2

3.4 g (0.002 mole) of 2-difluoromethylthiobenzaldehyde, 2.34 g (0.002 mole) of methyl ether of acetoacetic acid and 1,2 g (0.002 mole) of urea are dissolved in 20 ml of ethanol, then 2 ml of glacial acetic acid are added and the resultant mixture is left to stand overnight. The precipitate is then filtered and recrystallized from ethanol. The yield is 3.5 g (53%) of colourless crystals of 2-oxo-4-(2'-difluoromethylthiophenyl)-5-methoxycarbonyl-6-methyl-1,2,3,4-tetrahydropyrimidine. M.p. 211°–213° C. The product is identical with that produced in Example 1.

We claim:

1. 2-Oxo-4-(2'-difluoromethylthiophenyl)-5-methoxycarbonyl-6-methyl-1,2,3,4-tetrahydropyrimidine of the, formula:

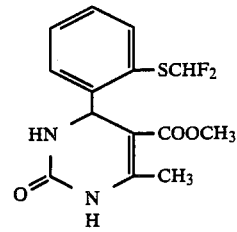

2. A pharmaceutical composition useful as as coronary-dilating agent, comprised of 2-Oxo-4-(2'difluoromethylthiophenyl)-5-methooxycarbonyl-6-methyl-1,2,3,4-tetrahydropyrimidine, having the formula:

and a pharmaceutically acceptable carrier.

3. A method of imparting a coronary dilating activity to a subject in need of such treatment, which comprises administering to said subject a coronary-dilating effective amount of the pharmaceutical composition of claim 2.

* * * * *